(12) United States Patent
Bonde et al.

(10) Patent No.: US 7,881,783 B2
(45) Date of Patent: Feb. 1, 2011

(54) IMPLANTABLE MEDICAL ELECTRICAL STIMULATION LEAD, SUCH AS A PNE LEAD, AND METHOD OF USE

(75) Inventors: Eric H. Bonde, Minnetonka, MN (US); Eric M. Stetz, Lino Lakes, MN (US); Carole A. Tronnes, Stillwater, MN (US)

(73) Assignee: Medtronics, Inc., Minneapolis, MN (US)

( * ) Notice: Subject to any disclaimer, the term of this patent is extended or adjusted under 35 U.S.C. 154(b) by 863 days.

(21) Appl. No.: 11/413,301

(22) Filed: Apr. 28, 2006

(65) Prior Publication Data

US 2007/0255370 A1 Nov. 1, 2007

(51) Int. Cl.
*A61N 1/05* (2006.01)
(52) U.S. Cl. ............................................. 607/2
(58) Field of Classification Search ............ 600/373, 600/374, 375, 377, 393; 607/2, 116, 119, 607/122, 123, 126, 127, 128
See application file for complete search history.

(56) References Cited

U.S. PATENT DOCUMENTS

| | | | | |
|---|---|---|---|---|
| 3,902,501 A | * | 9/1975 | Citron et al. | 607/126 |
| 4,716,888 A | * | 1/1988 | Wesner | 607/126 |
| 5,772,693 A | * | 6/1998 | Brownlee | 607/123 |
| 5,871,530 A | * | 2/1999 | Williams et al. | 607/122 |
| 6,055,456 A | * | 4/2000 | Gerber | 607/117 |
| 6,104,960 A | * | 8/2000 | Duysens et al. | 607/117 |
| 6,512,958 B1 | | 1/2003 | Swoyer et al. | |
| 6,847,849 B2 | | 1/2005 | Mamo et al. | |
| 6,971,393 B1 | | 12/2005 | Mamo et al. | |
| 6,999,819 B2 | | 2/2006 | Swoyer et al. | |
| 7,184,842 B2 | | 2/2007 | Seifert et al. | |
| 7,187,982 B2 | | 3/2007 | Seifert et al. | |
| 2003/0045919 A1 | | 3/2003 | Swoyer et al. | |
| 2006/0004429 A1 | * | 1/2006 | Mrva et al. | 607/116 |

OTHER PUBLICATIONS

K. Carlton et al., "Canine Evaluation of the InterStim® Tined Anchor: Acute Holding Strength," 4 pgs., 2002.
Medtronic Technical Manual entitled "InterStim®—Test Stimulation Lead Kit, For Use with Model 3625 Test Stimulator," 28 pgs., 2002.
Medtronic Instruction Manual entitled "InterStim®—Test Stimulation Components," 40 pgs., 2002.

* cited by examiner

*Primary Examiner*—Carl H Layno
*Assistant Examiner*—Frances P Oropeza (57) ABSTRACT

An implantable medical electrode lead for stimulation of bodily tissue. The lead is adapted for use with a needle lumen diameter of not greater than 0.05 inch, and includes a lead body and a tine assembly. The lead body has a distal section forming at least one exposed electrode surface. The tine assembly includes a plurality of tines each having a base end coupled to an exterior of the lead body immediately adjacent the exposed electrode surface and a free end that is movable relative to the lead body to inhibit axial migration of the lead body upon implantation into a patient. In one embodiment, the lead body is a PNE lead and provides two electrode surfaces for bipolar operation.

20 Claims, 10 Drawing Sheets

IMPLANTABLE MEDICAL ELECTRICAL STIMULATION LEAD, SUCH AS A PNE LEAD, AND METHOD OF USE

BACKGROUND OF THE INVENTION

The present invention relates to systems and methods for providing electrical stimulation to bodily tissue, such as a portion of a patient's nervous system. More particularly, it relates to temporarily implantable electrical leads, such as a peripheral nerve evaluation lead used to stimulate a sacral nerve, that resist migration and, in some embodiments, are bipolar.

A number of human bodily functions are affected by the nervous system. For example, bodily disorders, such as urinary incontinence, urinary urge/frequency, urinary retention, pelvic pain, bowel dysfunction (constipation, diarrhea, etc.), erectile dysfunction, etc., are all bodily functions influenced by the sacral nerves. As a point of reference, urinary incontinence is the involuntary loss of control over the bladder. Incontinence is primarily treated through pharmaceuticals and surgery. Many pharmaceuticals do not adequately resolve the issue and can cause unwanted side effects; further, a number of surgical procedures have a low success rate and/or are not reversible. Similar treatment insufficiencies have likewise been noted for many of the other maladies previously mentioned.

As an alternative to conventional pharmaceuticals and/or invasive surgical procedures, neurostimulation has more recently been recognized as a viable treatment approach for many patients. By way of background, the organs involved in bladder, bowel, and sexual function receive much of their control via the second, third, and fourth sacral nerves, commonly referred to as S2, S3, and S4, respectively. Electrical stimulation of these various nerves has been found to offer some control over these functions. Several electrical stimulation techniques have been suggested, including stimulation of nerve bundles within the sacrum. Regardless, in order to consistently deliver electrical stimulation to the sacral nerve(s), certain anatomical obstacles must be addressed. The sacrum is a large, triangular bone situated at the lower part of the vertebral column, and at the upper and back part of the pelvic cavity. The spinal canal runs through the greater part of the sacrum. Further, the sacrum is perforated by the anterior and posterior sacral foramina though which the sacral nerves pass.

With the above anatomical description in mind, partial control over one or more of the functions (or dysfunctions) previously mentioned has been achieved by implanting a neurostimulation lead at or near the sacral nerves. As a point of reference, other nerve(s) or tissue can similarly be electrically stimulated to produce different effects. Relative to sacral nerve stimulation, however, the neurostimulation lead, having several stimulation electrodes, can be permanently implanted within and/or anteriorly beyond the sacral foramen at which the sacral nerve in question is anatomically located. Because the lead, and in particular the stimulation electrodes, must remain in operative proximity to the sacral nerve, the permanent lead (sometimes referred to as a "chronic lead") can be sutured within the patient's body to resist migration. In light of the invasive nature associated with this approach, minimally invasive neurostimulation leads have been developed, incorporating features proximal the electrodes that inhibit migration and/or retrograde dislodgement. Permanent leads of this type are typically somewhat sizable to not only present a sufficient number of electrodes, but to also better resist migration. Regardless, wire cabling from the lead is implanted within a subcutaneously-formed tunnel and connected to a subcutaneously-implanted pulse generator. One example of such a system is available from Medtronic, Inc., of Minneapolis, Minnesota under the trade name InterStim®. Other chronic leads/systems are further described in U.S. Pat. Nos. 6,999,819; 6,971,393; and 6,847,849, each commonly assigned to the assignee of the present invention and the teachings of all of which are incorporated herein by reference.

Some patients may view the permanent neurostimulation lead and related pulse generator implantation described above as being a fairly traumatic procedure. Thus, efforts are conventionally made to ascertain in advance whether the patient in question is likely to receive benefit from sacral nerve stimulation. In general terms, the test stimulation procedure entails the temporary implantation of a neurostimulation lead in conjunction with an externally carried pulse generator or other power source. Once in place, the patient is exposed to neurostimulation over a trial period (e.g., 3-7 days) during which the patient can experience the sensation of nerve stimulation during various everyday activities, as well as record the changes, if any, in the bodily dysfunction of concern (e.g., a patient experiencing urinary incontinence can maintain a voiding diary to record voiding behavior and symptoms with the stimulation). The record of events is then compared with a base line and post-test stimulation diaries to determine the effect, if any, of sacral nerve stimulation on the symptoms being experienced by the patient. If the test stimulation is successful, the patient and his/her clinician can make a better informed decision as to whether permanent implantation and long-term sacral nerve stimulation is a viable therapy option.

Temporary implantation of the neurostimulation lead is normally done in one of two manners. With one approach, sometimes referred to as a "staged implantation," a conventional, permanent or chronic neurostimulation lead is implanted at the desired sacral location, with the cable carrying the coiled conductor wiring being externally extended through the patient's skin and coupled to the pulse generator. While viable, this technique entails the use of surgical equipment normally employed to permanently implant the stimulation lead. By way of background, implantation of a permanent sacral nerve stimulation lead normally requires the use of a fairly large introducer (e.g., an elongated, 13 gauge tube), and the chronic stimulation lead has a fairly large diameter. While local and/or general anesthesia is available, some patients may be apprehensive to participate in a short-term test of this type in view of the size of the instrument(s)/stimulation lead.

To better address the reluctance of some patients to participate in the stimulation test procedure described above, a second technique has been developed that entails the use of a smaller diameter, more simplified neurostimulation lead intended to be implanted on only a temporary basis. In general terms, the temporary stimulation lead (sometimes referred to as a peripheral nerve evaluation lead or "PNE" lead) has a single electrode and is of sufficiently small diameter so as to be percutaneously inserted using a small diameter needle (e.g., a 20 gauge needle). Many patients are not overly threatened by a small diameter needle and thus are more likely to participate in the trial stimulation. The percutaneous test stimulation is similar to an epidural nerve block, except that the temporary lead is inserted and left in the patient's back during the trial. The end of the lead that remains on the outside of the patient's body is secured to the patient's skin with, for example, surgical tape. Upon conclusion of the trial stimulation, the lead is removed from the patient.

While generally preferred by patients, the percutaneous, PNE lead technique may have certain drawbacks. For example, while the temporary simulation lead is highly capable of delivering the necessary stimulation energy throughout the evaluation period, it is possible that the lead may migrate. For example, any pulling or tugging on the proximal end of the lead body (from outside of the patient's body) could be directly communicated to the lead's electrode, thus creating a higher likelihood of electrode dislodgement and poor stimulation. Efforts have been made to address this concern, for example as described in U.S. Pat. No. 6,104,960, the teachings of which are incorporated herein by reference and assigned to the assignee of the present invention. In particular, a temporary neurostimulation lead is described as having a coiled configuration that better accommodates axial forces placed onto the lead body (e.g., tugging or pulling on the proximal end of the lead body). Any additional efforts to further minimize migration of the temporary neurostimulation lead would be well received, not only in the one exemplary context of peripheral sacral nerve electrical stimulation, but also for any other procedure in which an implantable medical electrical stimulation lead is used. Further, conventional PNE-type leads incorporate only one electrode (i.e., a unipolar lead electrode), such that a return electrode (or ground pad) is typically applied to the patient's skin. The ground pad may cause the patient some discomfort, and in some instances can become dislodged or disconnected during the test period, thus preventing the test stimulation therapy from occurring.

In light of the above, a need exists for a medical electrical lead which may be safely and effectively implanted in a minimally invasive manner, but which better inhibits axial migration of dislodgement of the lead body from the stimulation site, such as a sacral location. Other needs exist for bipolar PNE-type leads.

SUMMARY OF THE INVENTION

Aspects in accordance with principles of the present invention relate to an implantable medical electrode lead for applying electrical stimulation to bodily tissue. The implantable medical electrode lead is adapted to be introduced through and released into bodily tissue via a needle having a needle lumen defining a diameter of not greater than 0.05 inch. With this in mind, the lead includes a lead body and a tine assembly. The lead body has a proximal section adapted to be electronically coupled to a power source and a distal section forming at least one exposed electrode surface. The tine assembly includes a plurality of tines each having a base end and a free end. The tine assembly is associated with the lead body such that the base end of at least one of the tines is coupled to an exterior of the lead body immediately adjacent the exposed electrode surface. With this configuration, the free end of the at least one tine is movable relative to the lead body. With this construction, the tines are adapted to inhibit axial migration of the lead body upon implantation into a patient. In one embodiment, the tines are highly pliable. In other embodiments, the lead body is configured to provide two, longitudinally spaced and electrically isolated electrode surfaces such that the lead can be operated as a bipolar lead.

Other aspects in accordance with principles of the present invention relate to a system for providing temporary medical electrical stimulation to bodily tissue of a patient. The system includes a hollow needle and a flexible lead. The hollow needle defines a lumen having a diameter of not more than 0.05 inch. The flexible lead is slidably disposed within the lumen, and includes a lead body and a tine assembly. The lead body includes a proximal section adapted to be electrically coupled to a power source (e.g., an external pulse generator), and a distal section forming at least one exposed electrode surface. The tine assembly is associated with the lead body and includes a plurality of tines each having a base end and a free end. With this in mind, the base end of at least one of the tines is coupled to an exterior of the lead body immediately adjacent the exposed electrode surface such that the free end thereof is movable relative to the lead body. With this configuration, the system is adapted to promote minimally invasive insertion of the flexible lead, with the tine assembly inhibiting migration of the exposed electrode surface following insertion. In one embodiment, the lead body includes one or more coiled wires combining to define a central passage, with the system further including a stylet slidably disposed within the passage.

Yet other aspects in accordance with principles of the present invention relate to a method of providing temporary electrical stimulation to bodily tissue of a patient at a stimulation site. The method includes providing a flexible lead including a lead body and at least one tine assembly. The lead body has a proximal section and a distal section, with the distal section forming at least one electrode surface. The tine assembly includes a plurality of tines each having a base end and a free end. The tine assembly is associated with the lead body such that the base end of at least one of the tines is coupled to an exterior of the lead body immediately adjacent the exposed electrode surface, with the free end thereof being moveable relative to the lead body. Further, a hollow needle having a proximal end, distal end, and lumen is provided, with the needle lumen having a diameter not greater than 0.05 inch. The flexible lead is slidably inserted within the needle lumen. The needle is percutaneously directed toward the stimulation site, and the lead body is deployed and implanted at the stimulation site. To this end, the exposed electrode surface and the tine assembly are located at or within the stimulation site. A stimulation energy is applied to the exposed electrode surface via a power source electrically coupled to the lead body. In this regard, the tine assembly inhibits axial migration of the lead body. In one embodiment, the method is performed as part of a sacral nerve stimulation procedure, with the stimulation site being a sacral foramen. In a related embodiment, the method is characterized by the tine assembly interfacing with sacral bone. In other embodiments, energies are applied to the distal section of the lead body in a bipolar mode.

DETAILED DESCRIPTION OF THE INVENTION

Figure 1:
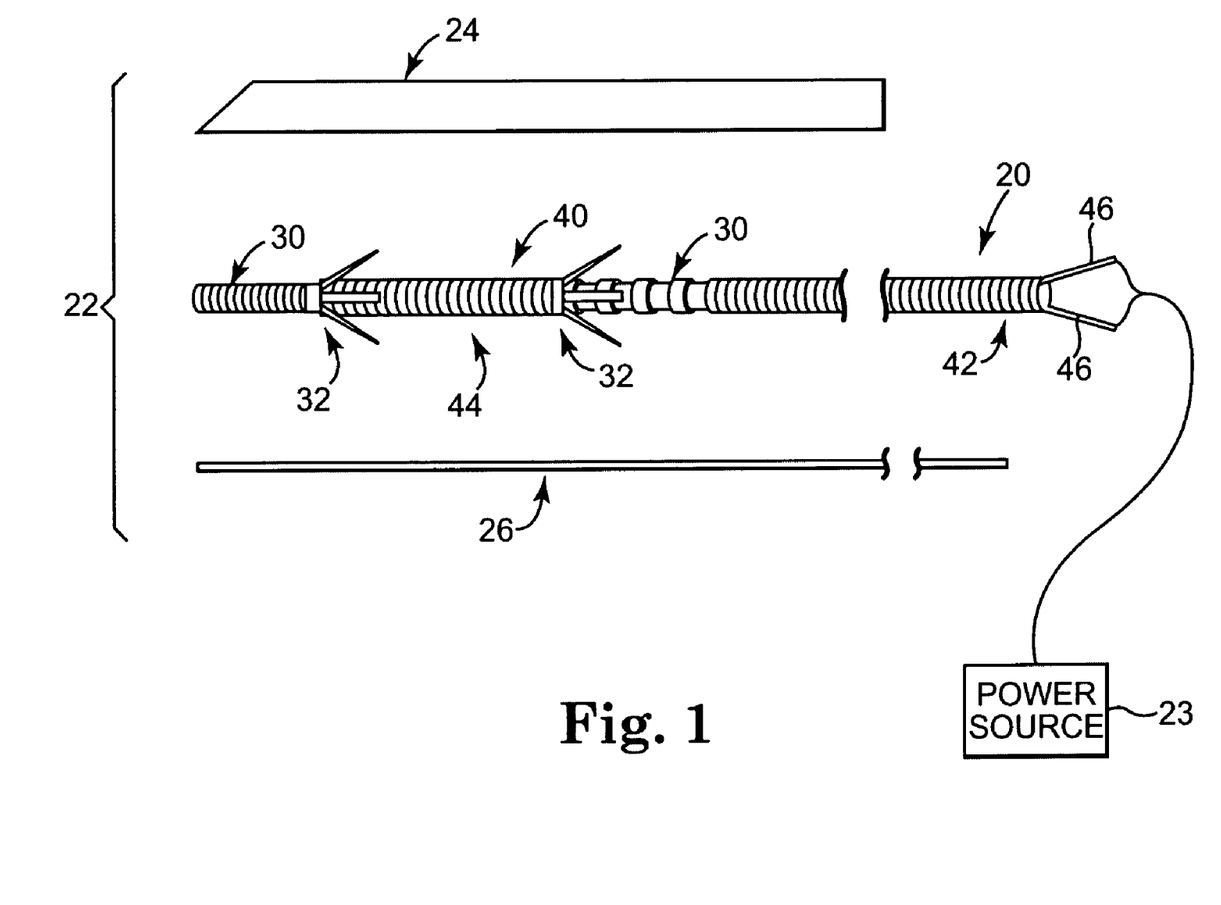
FIG. 1 is a simplified plan view of a system for providing electrical stimulation to bodily tissue of a patient, including an implantable medical electrical lead in accordance with principles of the present invention.

One embodiment of a medical electrical lead 20 in accordance with principles of the present invention is shown in simplified form in FIG. 1 as part of a system 22 useful for delivering stimulation energy to a patient (not shown) via a power source 23 (that may or may not be considered part of the system 22). The system 22 can assume a variety of forms, and can include components apart from those shown in FIG. 1. In one embodiment, however, the system 22 includes the lead 20, as well as a needle 24 and a stylet 26. Details on the various components are provided below.

In general terms, however, the lead 20 forms at least one exposed electrode surface 30, and is sized to be slidably received within the needle 24. The stylet 26 is sized to be slidably received within the lead 20. Finally, the power source 23 is electrically coupled to the lead 20 for providing electrical stimulation to the exposed electrode surface(s) 30. As described in greater detail below, the lead 20 is of a reduced size, amenable to being introduced to a delivery site (e.g., sacral foramen) through a relatively small-diameter needle 24 (for example, and as described below, a 20 gauge needle or other needle having an inner diameter no greater than 0.05 inch). Further, the lead 20 includes one or more tine assemblies 32 that inhibit migration of the lead 20 once implanted.

Figure 2A:
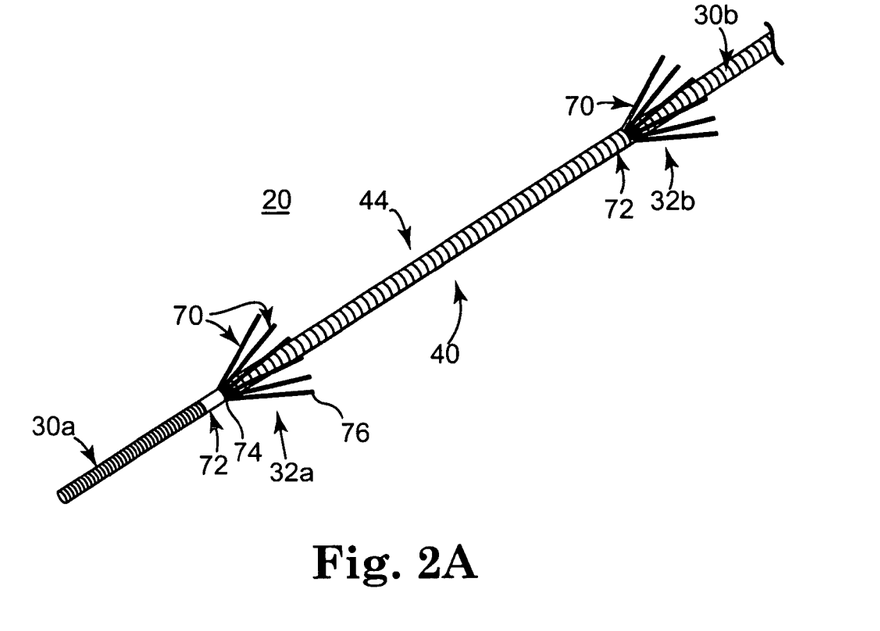
FIG. 2A is an enlarged, perspective view of a portion of one embodiment of the lead of FIG. 1.
Figure 2B:
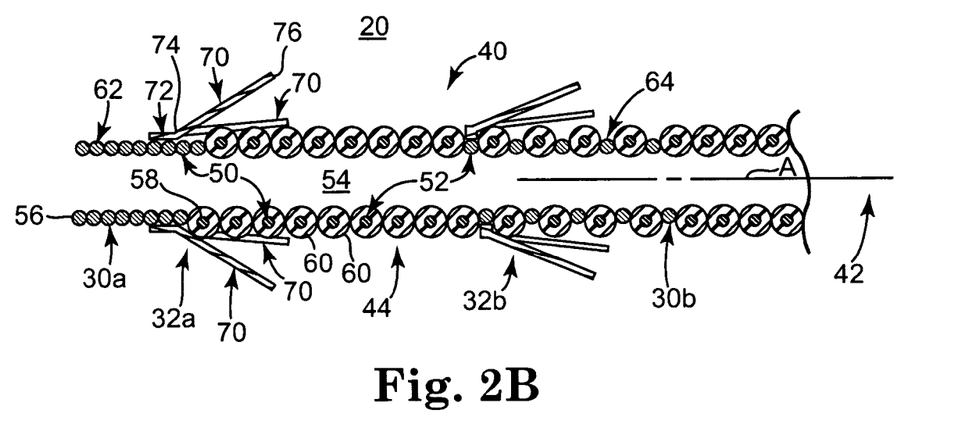
FIG. 2B is a cross-sectional view of the distal end of the lead of FIG. 2A.

One embodiment of the lead 20 is shown in greater detail in FIGS. 2A and 2B. The lead 20 includes a lead body 40 having a proximal section 42 (referenced generally in FIG. 2B; shown in greater detail in FIG. 1) and a distal section 44. The proximal section 42 is adapted to be electrically connected to the power source 23 (FIG. 1) for example via one or more connector pins 46 (FIG. 1). Conversely, the distal section 44, with the one embodiment of FIGS. 2A and 2B, forms a plurality of the exposed electrode surfaces 30, including the electrode surfaces 30a and 30b (referenced generally). As described in greater detail below, by providing the two exposed electrode surfaces 30a and 30b in a longitudinally spaced and electrically isolated arrangement, the lead 20 of FIGS. 2A and 2B is operable in a bipolar mode (e.g., the second exposed electrode surface 30b serves as a return or ground path for electrical current applied at the first exposed electrode surface 30a). Regardless, the lead 20 further includes a plurality of the tine assemblies 32, including a first tine assembly 32a and a second tine assembly 32b.

The lead body 40 is, in one embodiment, akin to a PNE lead having a relatively small maximum outer diameter (e.g., not greater than 0.05 inch, more preferably not greater than 0.04 inch, even more preferably not greater than 0.03 inch, and in one embodiment on the order of 0.025 inch, although other dimensions are also acceptable), such that the lead 20 can be implanted using a small diameter needle (e.g., the needle 24 (FIG. 1) can have a lumen diameter corresponding with the outer diameters specified above, for example as found with conventional 20 gauge or 19 gauge foramen needles). With this in mind and with specific reference to FIG. 2B, in one embodiment the lead body 40 includes first and second wires 50, 52 that are each wound in coil form (along at least the distal section 44), combining to form a lumen 54. In one embodiment, the first and second wires 50, 52 are co-axially inter-wound relative to one another, with a distal end 56 of the first wire/coil 50 extending distal a distal end 58 of the second wire/coil 52. Both of the wires 50, 52 can be closely wound as shown; in other embodiments, one or both of the wires 50, 52 can have a slight spacing between individual windings. Further, the coiled nature of the wires 50, 52 can be continued along the proximal section 42; alternatively, the wires 50, 52 can be straight or non-coiled proximal the distal section 44. Regardless, each of the wires/coils 50, 52 are formed of an electrically conductive material (e.g., stainless steel such as SST 316L stainless steel multi filament wire, MP35N alloy, etc.) such that electrical energy applied to the proximal section 42 readily conducts to the distal section 44 along each of the wires 50, 52. The coiled configuration of the wires 50, 52 along the distal section 44 imparts a longitudinal strain relief attribute to the lead body 40 such that any tugging or pulling on the proximal section 42 will not automatically be translated to the electrode(s) 30a and/or 30b.

Portions of each of the wires/coils 50, 52 are coated or exteriorly covered by an electrically non-conductive or insulative material 60. In one embodiment, the non-conductive material 60 is ETFE (a polymer of tetrafluoroethylene and ethylene), although other materials such as PTFE, polyurethane, fluoropolymers, silicone rubber, polyester, etc., are also useful. Further, while FIG. 2B illustrates the non-conductive material 60 as encircling or encompassing a circumference of the wires 50, 52, in other embodiments, the non-conductive material 60 can be applied to a lesser extent.

Regardless of the material and manufacturing technique selected, at least one region 62 (referenced generally) of the first wire/coil 50 and at least one region 64 (referenced generally) of the second wire/coil 52 are not covered by the non-conductive material 60, thus defining the exposed electrode surfaces 30a, 30b. For example, in one embodiment, the uncovered region 62 of the first wire/coil 50 is defined by simply not coating the non-conductive material 60 to that region (e.g., the non-conductive material 60 is applied to a portion of a length of the wire 50 prior to coiling), whereas the uncovered region 64 of the second wire/coil 52 can be formed by first coating an entirety of the second wire/coil 52 with the non-conductive material 60, and then removing (e.g., etching) the non-conductive material 60 from a portion of the second wire/coil 52 so as to define the uncovered region 64. Alternatively, a wide variety of other manufacturing techniques are also available.

The tine assemblies 32a, 32b are associated with the lead body 40 with at least one of the tine assemblies 32a and/or 32b being in close proximity to at least one of the exposed electrode surfaces 30a and/or 30b. In one embodiment, the tine assemblies 32a, 32b are highly similar in construction, such that the following description of the tine assembly 32a applies equally to the second tine assembly 32b. With this in mind, the tine assembly 32a includes, in one embodiment, a plurality of tines 70 and a band 72. Each of the tines 70 defines a length from a base end 74 to a free end 76 (as a point of reference, the base end 74 and the free end 76 are identified for one of the tines 70 in each of FIGS. 2A and 2B). The base end 74 of each the tines 70 is connected to the band 72 that in turn is coupled or affixed to the lead body 40. With this configuration, then, the tines 70 are movable relative to the lead body 40 whereby the free end 76 of each of the tines 70 is capable of splaying or extending radially outwardly relative to a central axis A defined by the distal section 44.

As a point of reference, the tines 70 are shown in FIG. 2A as being splayed away from the lead body 40 for purposes of illustration. In one embodiment, however, the tine assemblies 32, and in particular the tines 70, are highly pliable due to one or both of a material selection and/or thickness. In one embodiment, the highly pliable nature of the tines 70 is a function of the material selected; in one embodiment, the tine assemblies 32 are formed of a soft polymeric material such as polyurethane, silicone, PTFE, polyester, etc. With this configuration, then, apart from having an initial orientation in which the free end 76 of each of the tines 70 is positioned proximal the corresponding base end 74, the tines 70 do not have a predetermined spatial orientation in the absence of an external force. In other words, the tines 70 do not, in one embodiment, have shape memory or other attributes that would otherwise cause the tines 70 to automatically or self-revert to the orientation reflected in FIG. 2A. Stated otherwise, in the absence of an external force directing the free end 76 away from the lead body 40 (e.g., where the free end 76 is in contact with bodily tissue and the lead body 40 is pulled or forced in a proximal direction) extension of the tine 70 from the lead body 40 relative to the central axis A defines an angle of no more than 15°, more preferably no more than 10°, in a natural state of the lead 20. In other embodiments, however, the tine 70 can have a shape memory attribute otherwise causing the tines 70 to extend in a generally radially outward fashion relative to the lead body 40.

In one embodiment, at least one of the tine assemblies 32a and/or 32b is assembled to the distal section 44 of the lead body 40 in highly close proximity to one of the exposed electrode surfaces 30a, 30b. For example, with the one embodiment of FIGS. 2A and 2B, the first tine assembly 32a is positioned in highly close proximity to the first exposed electrode surface 30a, whereas the second tine assembly 32b is in highly close proximity to the second exposed electrode surface 30b. With specific reference to the tine assembly 32a, the band 72 is coupled to the uncovered region 62 of the first wire/coil 50, it being understood that where the tine assembly 32a/band 72 is formed of an electrically non-conductive material (e.g., akin to the non-conductive material 60), the band 72 effectively serves as a short extension of the non-conductive material 60, resulting in the exposed electrode surface 30a as shown (i.e., a longitudinal length of the exposed electrode surface 30a is less than a longitudinal length of the uncovered region 62). Where the tine assembly 32a is formed of a polymeric material, the exposed metal wire associated with the uncovered region 62 provides a surface highly amenable to bonding with the band 72 (otherwise formed of a polymeric material) via an appropriate adhesive. 1321 Regardless, the base end 74 of at least one, preferably all, of the tines 70 is thus coupled to the lead body 40 immediately adjacent the first exposed electrode surface 30a (i.e., the base end 74 is longitudinally spaced from the exposed electrode surface 30a by a distance of no more than 0.125 inch; more preferably no more than 0.065 inch; even more preferably no more than 0.03125 inch). In fact, in some embodiments, the base end 74 of at least one, preferably all, of the tines 70 can be affixed onto the first exposed electrode surface 30a (along a length thereof), for example where the band 72 is not included. Further, while with the one embodiment of FIGS. 2A and 2B the first tine assembly 32a is located proximal the first exposed electrode surface 30a, in other embodiments, one or more of the tine assemblies 32 can be positioned distal, preferably immediately distal, the first exposed electrode surface 30a. For example, the second tine assembly 32b is formed distal the second exposed electrode surface 30b, with the base end 74 of each of the tines 70 associated with the second tine assembly 32b being coupled to the distal section 44 immediately adjacent the second exposed electrode surface 30b as previously described. As described in greater detail below, positioning of the tine assemblies 32 in accordance with this one embodiment enhances an ability of the lead 20 to resist migration following implantation.

While the tine assemblies 32 are shown in FIG. 2A as each including four of the tines 70, any other number, either greater or lesser, can be provided. Further, while the tine 70 associated with each of the tine assemblies 32 are illustrated as being approximately equidistantly spaced about a circumference of the lead body 40, a non-equidistant spacing can also be employed.

The tine assemblies 32 can be formed in a wide variety of fashions. In one embodiment, for example, the tine assemblies 32 are formed from an extruded tubing that is then cut to define the tines 70 (with the uncut portion forming the band 72). Alternatively, the tine assemblies 32 can be formed by capturing a plurality of strands (e.g., sutures strands) under a small section of tubing that is otherwise assembled to the lead body 40. With this configuration, then, the strands define the tines 70, whereas the small section of tubing forms the band 72. Other construction techniques, such as providing the tine assembly 32 as a molded component, are also acceptable. Regardless, the tine assemblies 32 can be assembled to the lead body 40 as previously described (i.e., use of an adhesive to bond the band 72 to metal associated with the respective uncovered regions 62, 64 of the first and second wires 50, 52). Alternatively, one or more of the tine assemblies 32 can be adhered to the non-conductive material 60 with an appropriate adhesive; shrink-fitting the tine assemblies 32 over the lead body 40 (e.g., at or along the respective uncovered regions 62 or 64, and/or over the non-conductive material 60); etc.

Figure 3A:
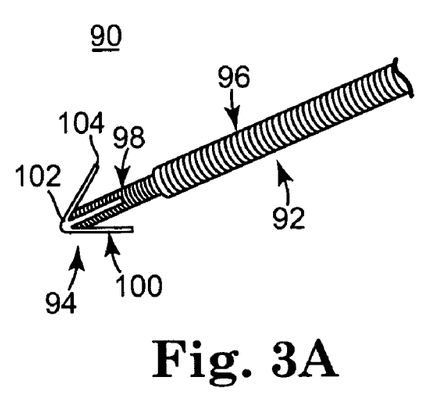
FIG. 3A is an enlarged, perspective view of an alternative embodiment lead in accordance with principles of the present invention.
Figure 3B:
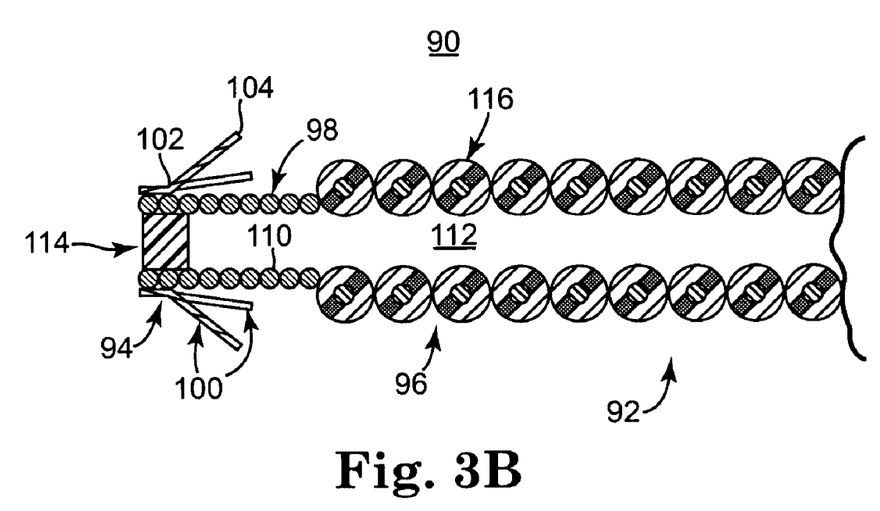
FIG. 3B is a cross-sectional view of a portion of the lead of FIG. 3A.

While the lead 20 has been described as including a plurality of the exposed electrode surfaces 30 and a plurality of the tine assemblies 32, in other embodiments, a single one of the exposed electrode surfaces 30 and/or the tine assemblies 32 can be provided. For example, FIGS. 3A and 3B illustrate an alternative embodiment lead 90 in accordance with principles of the present invention. The lead 90 includes a lead body 92 and a tine assembly 94. The lead body 92 defines a proximal section (not shown) and a distal section 96, with the distal section 96 forming an exposed electrode surface 98. Similar to previous embodiments, the tine assembly 94 includes a plurality of tines 100 each having a base end 102 and a free end 104. The tine assembly 94 is coupled to the lead body 92 such that the base end 102 of at least one, preferably all, of the tines 100 are immediately adjacent the exposed electrode surface 98.

As best shown in FIG. 3B, the lead body 92 is defined by a wire 110 wound as a coil (at least along the distal section 96) to define a lumen 112. Once again, the lumen 112 is sized to slidably receive the stylet 26 (FIG. 1). With the one embodiment of FIG. 3B, the lead 90 further includes a core 114 comprised of, in one embodiment, a solid cylindrical stainless steel material (or other materials such as MP35N, PtIr, etc. The wire/coil 110 is crimped to the core 114; to this end, a crimp skirt (not shown) can be employed at an exterior of the wire/coil 110 to ensure assembly of the core 114. The core 114 closes the lumen 112 so as to inhibit passage of the stylet 26 distally through the lead body 92. In one embodiment, the core 114 can be configured to elute a therapeutic substance (e.g., a pharmacologic agent, such as the steroid dexamethasone). In yet other embodiments, the core 114 can be eliminated.

Regardless of whether the core 114 is provided, a portion of the wire/coil 110 is encompassed by an electrically non-conductive material 116 (akin to the non-conductive material 60 (FIGS. 2A and 2B) previously described) so as to define the exposed electrode surface 98. The resultant lead body 92 has, in some embodiments, a relatively small outer diameter (e.g., in accordance with the dimensions recited above with respect to the lead body (FIG. 2B)), such that the lead body 92 is akin to a convention PNE lead, appropriately sized for deployment via a small diameter needle (e.g., a 19 or 20 gauge foramen needle). Further, by forming only the one electrode surface 98, the lead 90 of FIGS. 3A and 3B is a unipolar lead. In alternative constructions, the lead body 92 can be comprised of two or more components that combine to define the exposed electrode surface 98, whereas a remainder of the lead body 92 does not conduct energy from an external surface thereof.

As previously described, the tine assembly 94 can assume any of the configurations previously provided with respect to the tine assemblies 32a, 32b (FIGS. 2A and 2B). Regardless, with the one embodiment of FIGS. 3A and 3B, the tine assembly 94 is associated with the lead body 92 such that at least one, preferably all, of the tines 100 are positioned distal (and/or immediately adjacent) at least a portion of the exposed electrode surface 98.

Figure 4A:
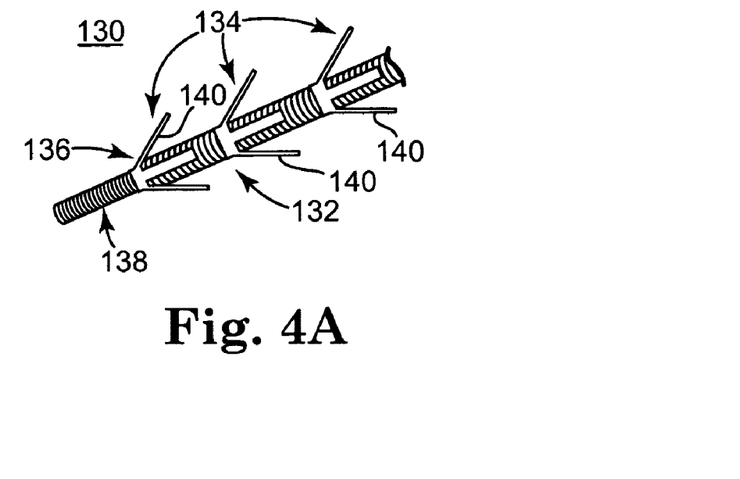
FIG. 4A is an enlarged, perspective view of an alternative embodiment lead in accordance with principles of the present invention.
Figure 4B:
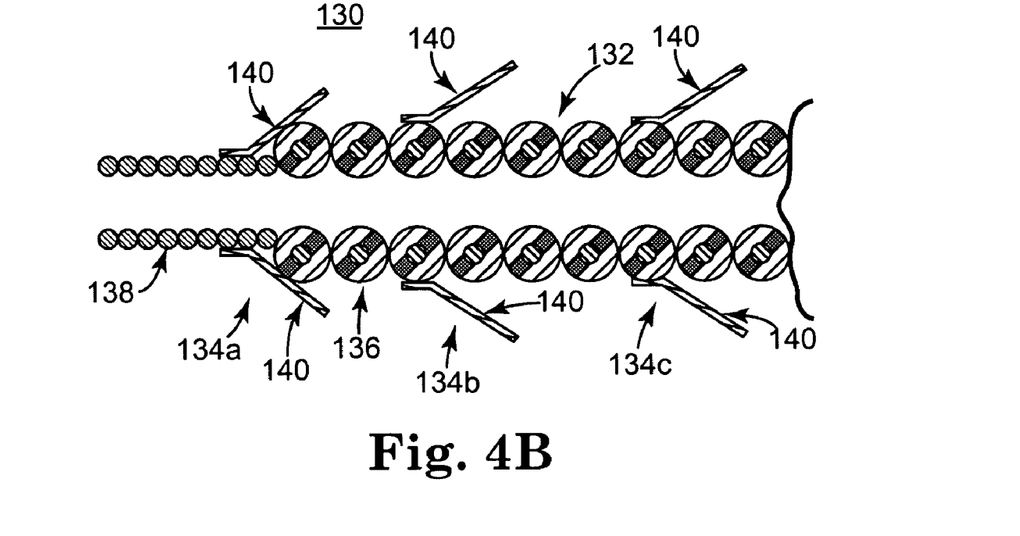
FIG. 4B is a partial, cross-sectional view of the lead of FIG. 4A.

Yet another alternative embodiment lead 130 in accordance with principles of the present invention is shown in FIGS. 4A and 4B. Once again, the lead 130 includes a lead body 132 and a plurality of tine assemblies 134 (referenced generally in FIG. 4A). The lead body 132 includes a proximal section (not shown) and a distal section 136 otherwise providing an exposed electrode surface 138. Similar to the embodiment of FIGS. 3A and 3B, the lead body 132 of FIGS. 4A and 4B provides one exposed electrode surface 138, and thus is suited for operation in a unipolar manner (that might otherwise require a separate return electrode (not shown)).

Regardless, the plurality of tine assemblies 134 are similar to previous embodiments, and include first-third tine assemblies 134a-134c (identified in FIG. 4B), each including a plurality of tines 140.

The first or distal-most tine assembly 134a is associated with the lead body 132 such that at least one, preferably all, of the tines 140 associated therewith are positioned immediately adjacent the exposed electrode surface 138 as previously described. The second and third tine assemblies 134b, 134c are longitudinally spaced from the exposed electrode surface 130. With this one embodiment, then, at least one of the tine assemblies 134 (i.e., the first tine assembly 134a) is positioned immediately adjacent the exposed electrode surface 138, whereas one or more of the tine assemblies 134 (e.g., the third tine assembly 134c) is not immediately adjacent the exposed electrode surface 138, but instead is longitudinally spaced therefrom (e.g., by a longitudinal distance of at least 0.125 inch).

Figure 5A:
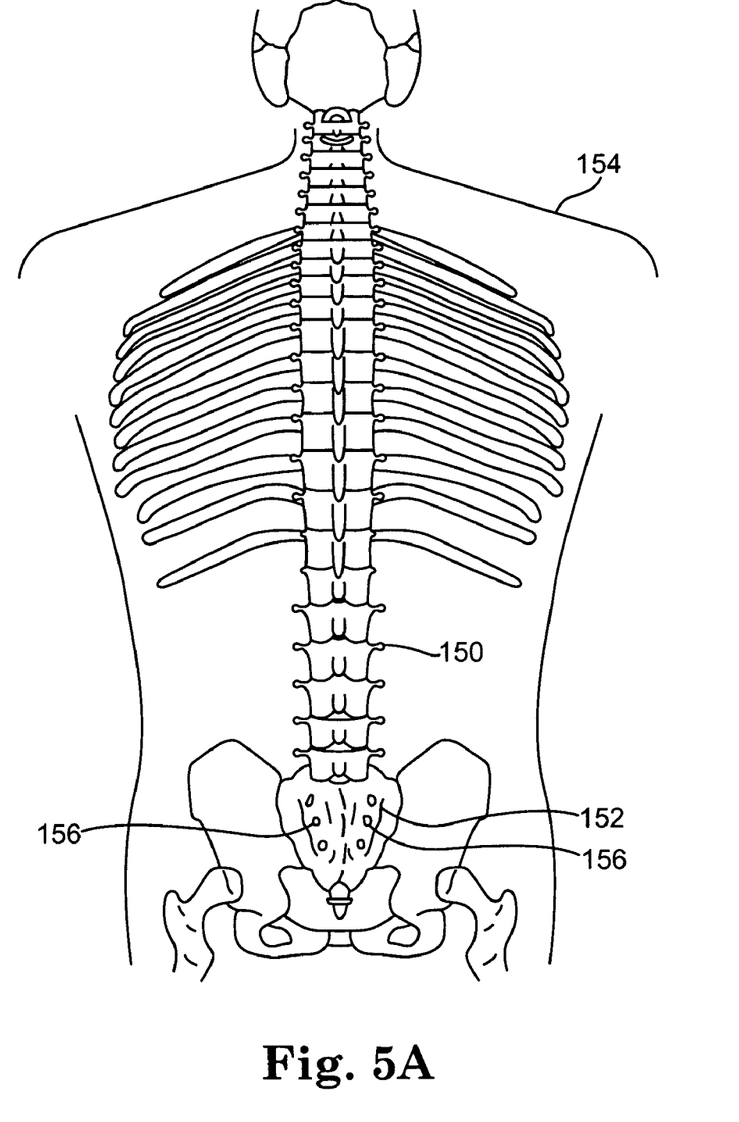
FIG. 5A is a posterior view of a spinal column of a patient, showing a location of a sacrum relative to an outline of a body.
Figure 5B:
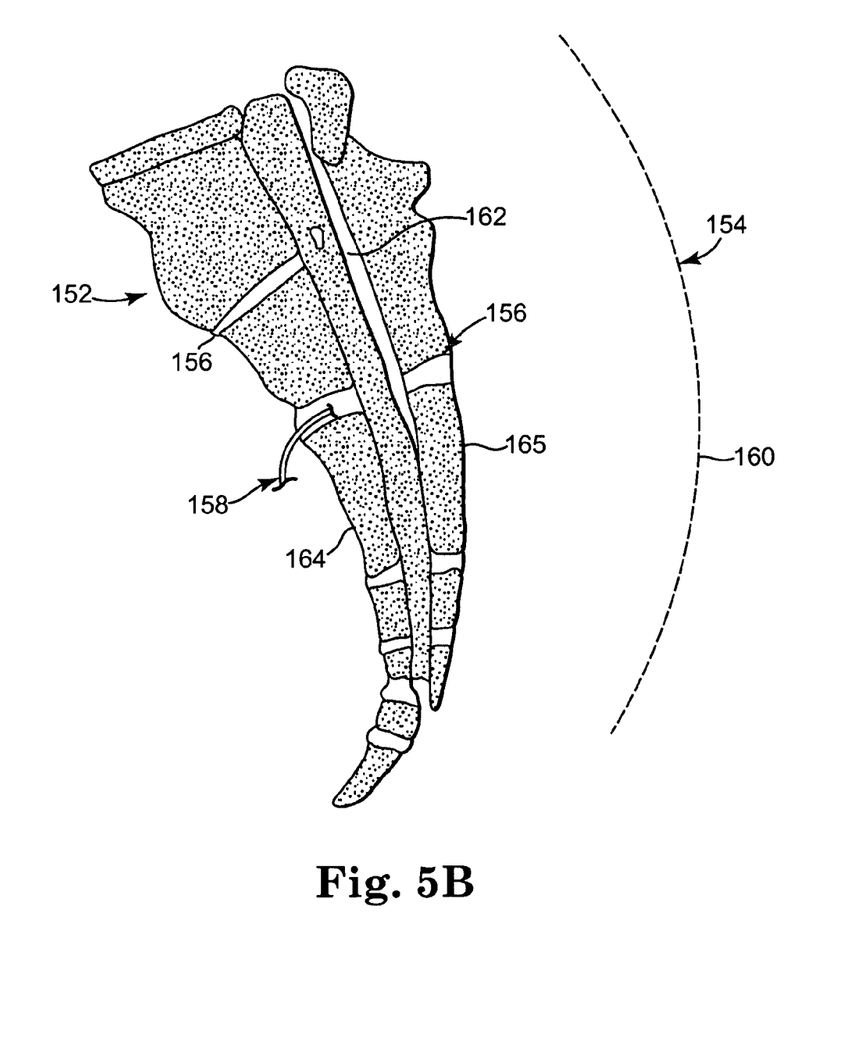
FIG. 5B is a simplified sectional view of a human anatomy in a region of the sacrum.

Returning to FIG. 1, the system 22, and in particular the lead 20 (or the lead 90 (FIGS. 3A and 3B) or the lead 130 (FIGS. 4A and 4B)), in accordance with principles of the present invention can be utilized to provide medical electrical stimulation from the external power source 23 to a wide variety of bodily structures via a percutaneous approach. For example, the system 22 can be deployed to stimulate one or more nerves of the nervous system. Alternatively, the system 22 can be used in other applications requiring electrical stimulation, such as procedures to rehabilitate muscle dysfunction by neuromodulation (e.g., functional electrical stimulation) of muscular behavior. In one embodiment, however, the system 22 is employed to provide electrical stimulation to a sacral nerve(s), for example as part of a peripheral sacral nerve simulation test or evaluation. With respect to this one exemplary application, FIG. 5A provides a posterior view of a spinal column 150 showing a location of a sacrum 152 relative to an outline of a patient's body 154. As shown, the sacrum 152 has a series of holes or foramen 156 therethrough. Each foramen 156 provides access to sacral ventral nerves (not shown). This relationship is further illustrated in FIG. 5B whereby sacral nerves (a peripheral sacral nerve of which is illustrated schematically and generally referenced at 158) extend along the sacrum 152, generally opposite a dorsal surface 160 of the patient's body 154, and through or from a sacral canal 162. FIG. 5B further illustrates a pelvic surface 164 and a dorsal surface 165 of the sacrum 152.

Figure 6:
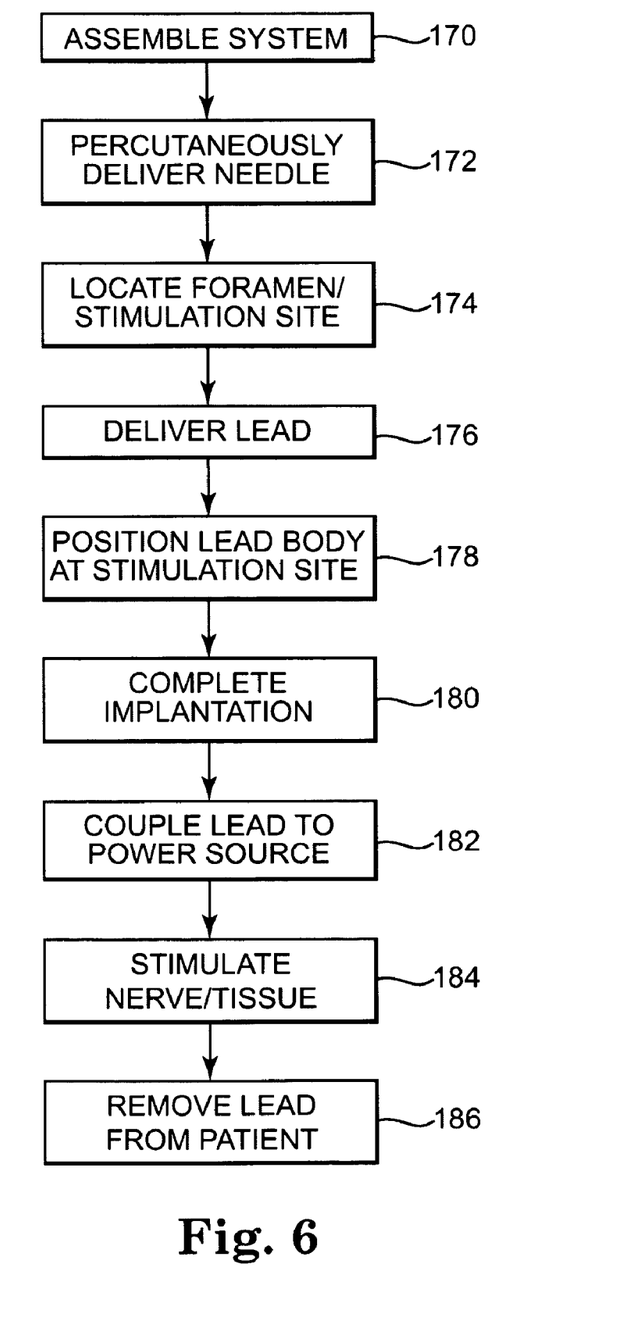
FIG. 6 is a flow diagram relating to a method of evaluating a peripheral nerve of a patient in accordance with principles of the present invention.
Figure 7A:
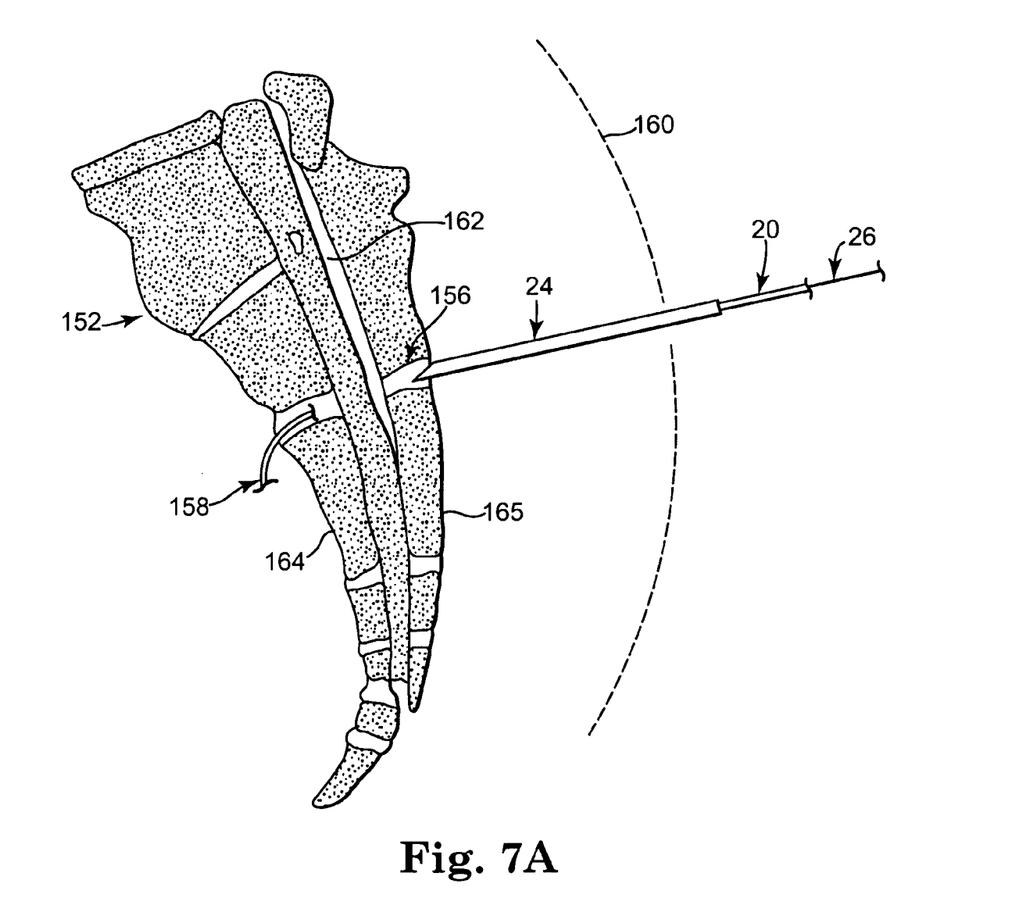
FIG. 7A-7C illustrate temporary implantation of the neurostimulation lead using the system of FIG. 1.
Figure 7B:
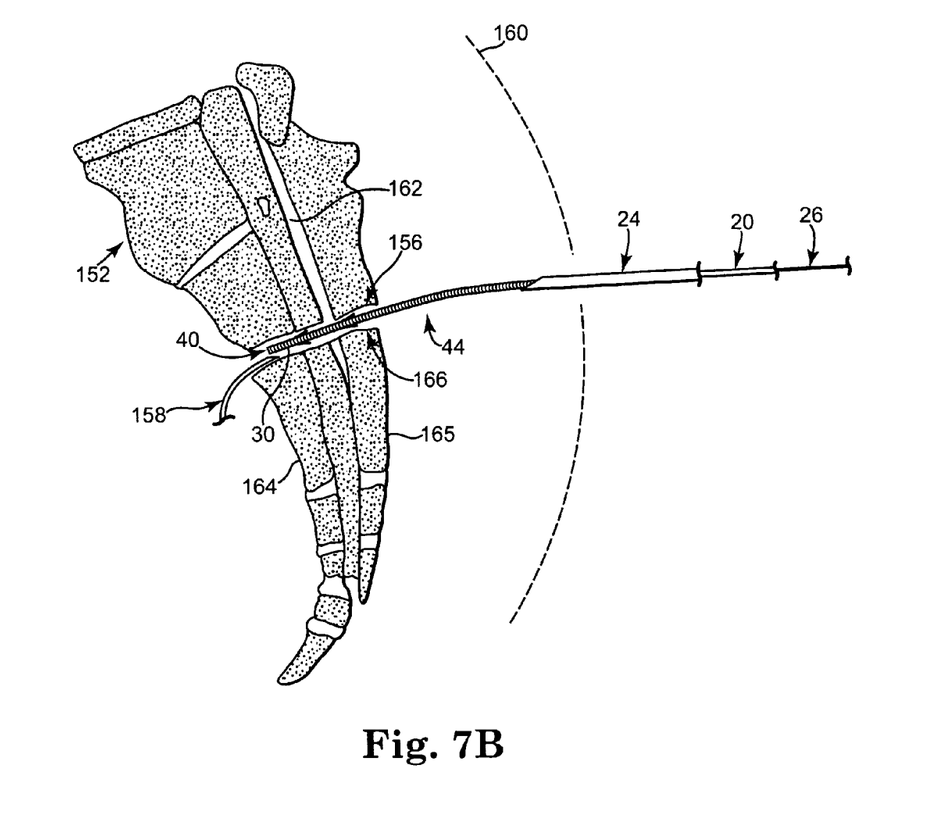
Figure 7C:
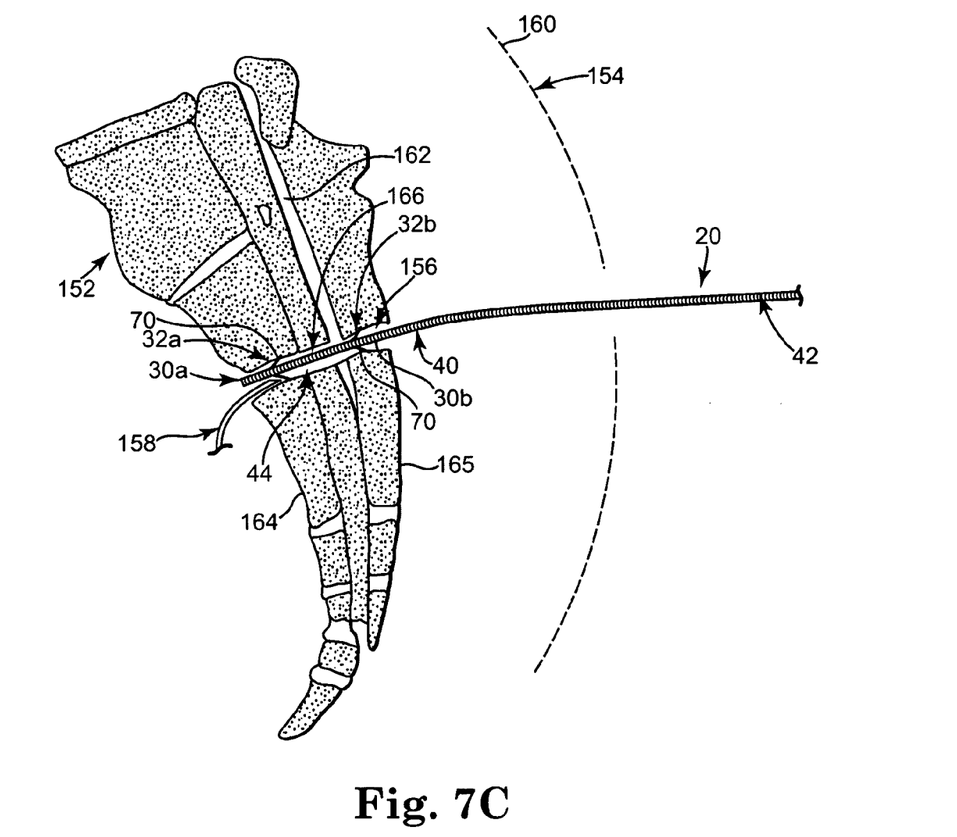

With the above anatomical conventions in mind, one method of evaluating a peripheral sacral nerve 158 in accordance with principles of the present invention is provided by the flow diagram of FIG. 6, as well as the illustrations of FIGS. 7A-7C. As a point of reference, the foregoing description relates to use of the lead 20 of FIGS. 2A and 2B, it being understood that the leads 90, 130 are equally applicable. At step 170, the system 22 is arranged such that a portion of the lead 20 is slidably received within the needle 24, and the stylet 26 is slidably received within the lumen 54 (FIG. 2B) of the lead body 40. As previously described, the lead body 40 has a relatively small diameter such that the needle 24 and its corresponding needle lumen can also be of a small diameter, for example, a 19 gauge or 20 gauge thin wall metal needle (e.g., the needle lumen diameter provided with 20 gauge foramen needles available from Medtronic, Inc., of Minneapolis, Minn. under product numbers 041828 or 041829). In one embodiment, the needle 24 is preferably insulated with a non-conductive coating (e.g., a parylene coating) along its outer surface except at a distal tip and a proximal end thereof. This permits the needle tip to electrically stimulate nerves to assess whether a desired location has been obtained by the needle tip during the implant procedure. Regardless, at step 172, the needle 24 is percutaneously delivered to the sacrum 152, and at step 174, one of the foramen 156 is located as shown in FIG. 7A, for example using conventional techniques (e.g., energizing a distal end of the needle 24 and observing physical reactions by the patient). As a point of reference, in some embodiment, location of the foramen 156 by the needle 24 prior to assembling the lead 20/stylet 26 within the needle lumen. Thus, step 170 can occur after step 174.

Once the foramen 156 is located, the distal section 44 of the lead 20 is delivered to and/or through the located foramen at step 176. In one embodiment, delivery of the distal section 44 of the lead 20 through the foramen 156 is achieved by distally advancing the lead 20 relative to the needle 24 as shown in FIG. 7B. To this end, the stylet 26 assists in achieving distal movement of the lead 20, serving to render the lead body 40 more rigid and thus capable of pushing through the foramen 156/bodily tissue.

At step 178, the lead body 40 is positioned at a desired location or stimulation site 166 (referenced generally) that is otherwise in operative proximity to one of the sacral nerves, such as the sacral peripheral nerve 158 in FIG. 7B. The operatively proximate position is characterized by the patient exhibiting a physical response to an electrical stimulation applied to the lead body 40 (and in particular, the exposed electrode surface 30) in a manner otherwise indicative of a sacral nerve being electrically stimulated. As a point of reference, precise positioning of the distal section 44 relative to the sacral nerve 158 in question is not required so long as once an operatively proximate position is achieved, the distal section 44 does not overtly migrate (i.e., axially migrate or dislodge back through the foramen 156). Thus, as shown in FIG. 7C, the lead body 40 can be positioned such that the exposed electrode surface 30 is in close proximity to the sacral nerve 158; alternatively, a spacing between the exposed electrode surface 30 and the sacral nerve 158 can be present. Regardless, in connection with directing the distal section 44 to the desired location 166, one or more of the tine assemblies 32 (for example, the distal tine assembly 32*a*) is inserted anterior beyond the dorsal surface 165 and can contact and/or nearly contact one or more of the sacral nerves (e.g., the sacral peripheral nerve 158). Due to the preferred, highly pliable construction of the tines 70, the sacral nerves 158 will not be damaged if contacted by the tine 70.

As shown in FIG. 7C, in the operatively proximate location 166, at least one of the tine assemblies 32 (e.g., the tine assembly 32*a*) is located adjacent the pelvic surface 164, with another of the tine assemblies 32 (e.g., the tine assembly 32*b*) being located within the foramen 156 and anteriorly beyond the dorsal surface 165. Thus, at step 180, whereby the implantation is completed and the proximal section 42 is secured (e.g., surgically taped) to an exterior of the patient's body 154, the tine assemblies 32 resist or impede axial dislodgement of the distal section 44 of the lead body 40 axially back through the foramen 156 by engaging or contacting the boney surfaces presented by the sacrum 152. For example, in one embodiment, at least one of the tines 70 associated with the distal-most tine assembly 32*a* contacts or abuts the sacrum 152 at or adjacent the pelvic surface 164, and in some embodiments is anteriorly beyond the pelvic surface 164. Further, one or more of the tine assemblies (e.g., the second tine assembly 32*b*) contacts the rigid boney material otherwise forming the foramen 156 within which the tine assembly 32*b* is located, for example within the sacral canal 162 and/or anteriorly adjacent the dorsal surface 165. Thus, by interfacing with rigid, boney structures, a more complete fixation of the lead 20 in the operatively proximate location (or stimulation site) 166 can be achieved. Further, the sacral foramen 156 is covered with a membraneous connective tissue along the dorsal side thereof, this tissue can provide an ideal surface to interact with the tines 70 and provide a level of fixation.

Once implanted, at step 182, the proximal section 42 is electrically coupled to the power source 23 (FIG. 1) that is otherwise located external the patient's body 154. The power source 23 can assume a wide variety of forms, but in one embodiment, is a pulse generator, for example a Model 3625 InterStim® Test Stimulator available from Medtronic, Inc., of Minneapolis, Minn.

Following the above-described implantation methodology, in one embodiment the implanted lead 20/external power source 23 is operated over the course of several or more days at step 184 to periodically electrically stimulate the sacral nerve 158. With the one embodiment of FIGS. 7A-7C, the lead 20, and in particular the lead body 40, provides a bipolar mode of operation via the first and second exposed electrode surfaces 30*a*, 30*b*. In other embodiments, however, the lead 20 can be of a unipolar design (i.e., providing only a single exposed electrode surface) such that a return electrode (not shown) is also provided and secured to the patient's skin. Following the test period, an evaluation can be made, based, for example, upon records kept by the patient during the test period, as to whether a permanently-implanted nerve stimulation system is a viable option.

Regardless, at step 186, upon completion of the test period, the lead 20 is removed from the patient by releasing the proximal section 42 from the patient's skin, and then applying a slight pulling or retraction force thereto. This retraction force removes the distal section 44 from the operatively proximate location 166 and back through the initial point of insertion through the patient's skin. In this regard, the tine assemblies 32*a*, 32*b* do not overtly resist this removal. For example, the tines 70 readily fold back over themselves (i.e., the tines 70 associated with the first tine assembly 32*a* will fold over onto themselves as the lead 20 is retracted through the foramen 156).

The medical electrical lead, and related system and method of use, of the present invention provides a marked improvement over previous designs. The lead is readily and temporarily implanted via a small diameter needle, thus addressing concerns raised by some patients. In addition, the tine assembly or assemblies inhibit axial migration of the lead body once implanted while presenting little or no opportunities for damaging the patient tissue contacted by the tine assemblies, for example nerves.

Although the present invention has been described with reference to preferred embodiments, workers skilled in the art will recognize that changes can be made in form and detail without departing from the spirit and scope of the present invention. For example, while the lead has been described as including or providing one or two electrodes, in other embodiments, a multiplicity of electrodes are carried by the lead.

What is claimed is:

1. An implantable medical electrode lead for applying electrical stimulation to bodily tissue of a patient and adapted to be introduced through, and released into, bodily tissue via a needle having a needle lumen defining an inner diameter of not greater than 0.05 inch, the lead comprising:
   a lead body having a proximal section adapted to be electronically coupled to a power source and a distal section forming at least one exposed electrode surface; and
   a first tine assembly adapted to inhibit axial migration of the lead body, wherein the tine assembly is associated with the lead body and includes a plurality of tines each having a base end and a free end, wherein the base end of at least one of the tines is coupled to an exterior of the lead body immediately adjacent the exposed electrode surface such that the free end is movable relative to the lead body, wherein the tine assembly comprises a tube cut to form the plurality of tines.

2. An implantable medical electrode lead for applying electrical stimulation to bodily tissue of a patient and adapted to be introduced through, and released into, bodily tissue via a needle having a needle lumen defining an inner diameter of not greater than 0.05 inch, the lead comprising:
   a lead body having a proximal section adapted to be electronically coupled to a power source and a distal section forming at least one exposed electrode surface; and
   a first tine assembly adapted to inhibit axial migration of the lead body, wherein the tine assembly is associated with the lead body and includes a plurality of tines each having a base end and a free end, wherein the base end of at least one of the tines is coupled to an exterior of the lead body immediately adjacent the exposed electrode surface such that the free end is movable relative to the lead body, wherein a spacing between the base end of at least one of the tines and an end of the exposed electrode surface is no more than 0.125 inch.

3. An implantable medical electrode lead for applying electrical stimulation to bodily tissue of a patient and adapted to be introduced through, and released into, bodily tissue via a needle having a needle lumen defining an inner diameter of not greater than 0.05 inch, the lead comprising:
   a lead body having a proximal section adapted to be electronically coupled to a power source and a distal section forming at least one exposed electrode surface, wherein the lead body includes a wire wound to form a first coil defining an internal passage; wherein the lead body includes a non-conductive material disposed over at least a portion of the coil to define a covered region and an uncovered region, and further wherein the exposed electrode surface is defined by the uncovered region;

wherein the lead body further includes a second wire wound to form a second coil, the first and second coils being co-axially wound to one another with a distal end of the second coil terminating proximal a distal end of the first coil, and further wherein the second coil forms a second exposed electrode surface proximal the exposed electrode surface formed by the first coil such that the lead body is capable of bipolar operation; and a first tine assembly adapted to inhibit axial migration of the lead body, wherein the tine assembly is associated with the lead body and includes a plurality of tines each having a base end and a free end, wherein the base end of at least one of the tines is coupled to an exterior of the lead body immediately adjacent the exposed electrode surface such that the free end is movable relative to the lead body.

4. The implantable lead of claim 3, wherein the lead body further includes a non-conductive material disposed over a portion of the second coil to define a covered region and an uncovered region, the second exposed electrode surface being defined by the uncovered region associated with the second coil.

5. The implantable lead of claim 4, wherein windings of the uncovered region of the second coil are sequentially located between windings of the covered region of the first coil.

6. A system for providing medical electrode stimulation to bodily tissue of a patient, the system comprising:
a hollow needle defining a lumen having a diameter of not more than 0.05 inch; and
a flexible lead slidably disposed within the needle lumen, the flexible lead including:
a lead body having a proximal section adapted to be electrically coupled to a power source and a distal section forming at least one exposed electrode surface,
a first tine assembly including a plurality of tines each having a base end and a free end,
wherein the base end of at least one of the tines is coupled to an exterior of the lead body immediately adjacent the exposed electrode surface such that the free end is movable relative to the lead body.

7. The system of claim 6, wherein the at least one tine is coupled to the lead body distal the exposed electrode surface.

8. The system of claim 6, wherein the distal section forms a plurality of longitudinally spaced exposed electrode surfaces, and further wherein the first tine assembly is coupled to the lead body longitudinally between two of the exposed electrode surfaces.

9. The system of claim 6, wherein the flexible lead further comprises:
a second tine assembly coupled to the lead body and longitudinally spaced from the first tine assembly in a proximal direction.

10. The system of claim 6, wherein the system is configured for performing a peripheral sacral nerve stimulation procedure, the lead being configured as a peripheral nerve evaluation lead and the needle being configured to percutaneously access a sacral foramen.

11. The system of claim 6, wherein the lead body includes first and second wire coils each defining an exposed electrode surface at the distal section, the exposed electrode surfaces being electrically isolated from one another to form a bipolar electrode array.

12. The system of claim 6, wherein the lead body forms a central passage, the system further comprising: a stylet slidably disposed within the central passage.

13. A method of providing temporary electrical stimulation to bodily tissue of a patient at a stimulation site, the method comprising:
providing a flexible implantable medical electrical lead including:
a lead body having a proximal section adapted to be electronically coupled to a power source and a distal section forming at least one exposed electrode surface,
a tine assembly including a plurality of tines, each having a base end and a free end,
wherein the base end of at least one of the tines is coupled to an exterior of the lead body immediately adjacent the exposed electrode surface such that the free end is movable relative to the lead body;
providing a hollow needle having a proximal end, a distal end, and a lumen defining a diameter of not greater than 0.05 inch;
slidably inserting the lead body within the needle lumen;
percutaneously directing the distal end of the needle toward the stimulation site;
deploying the lead body from the distal end of the needle to implant the lead body at the stimulation site, wherein the tine assembly is located within the stimulation site; and
applying energy to the exposed electrode surface via a power source to electrically stimulate tissue at the stimulation site; wherein the tine assembly inhibits axial migration of the lead body from the stimulation site.

14. The method of claim 13, further comprising:
temporarily implanting the distal section of the lead body at the stimulation site;
connecting the proximal portion of the lead body to a pulse generator; and
maintaining the pulse generator external the patient.

15. The method of claim 13, wherein deploying the lead body from the distal end of the needle includes passing the tine assembly at least partially through the stimulation site.

16. The method of claim 13, wherein the lead body includes a second exposed electrode surface, and further wherein applying energy includes operating the lead body as a bipolar electrode.

17. The method of claim 13, wherein the method is performed as part of a sacral nerve stimulation procedure, and further wherein percutaneously directing the distal end of the needle toward the stimulation site includes locating a sacral foramen with the distal end of the needle.

18. The method of claim 17, wherein deploying the lead body includes directing the tine assembly into a sacral foramen.

19. The method of claim 17, wherein deploying the lead body includes directing the tine assembly distally beyond a peripheral sacral nerve.

20. The method of claim 17, wherein deploying the lead body at the stimulation site is characterized by one or more of the tines interfacing with sacral bone anterior a dorsal surface of the sacrum.

* * * * *